United States Patent [19]

Hojo et al.

[11] Patent Number: 4,732,605

[45] Date of Patent: Mar. 22, 1988

[54] PLANT GROWTH REGULATOR COMPOSITION

[75] Inventors: Shiro Hojo, Tokyo; Eiichi Kimura, Takamatsu; Tetsuji Iwasaki, Wakayama, all of Japan

[73] Assignees: Kao Corporation; Japan Hydrazine Company, Inc., both of Tokyo, Japan

[21] Appl. No.: 938,829

[22] Filed: Dec. 8, 1986

[30] Foreign Application Priority Data

Dec. 25, 1985 [JP] Japan ................... 60-296130

[51] Int. Cl.$^4$ ............... A01N 43/58; A01N 41/10
[52] U.S. Cl. ................................ 71/92; 71/78; 71/103
[58] Field of Search ............ 71/92, 98, 103, 111, 71/121

[56] References Cited

U.S. PATENT DOCUMENTS 2,614,916 10/1952 Hoffman et al. ............... 71/92
4,369,057 1/1983 Takeno et al. ................. 71/92

FOREIGN PATENT DOCUMENTS 133289 5/1977 Japan ................... 71/103
120622 5/1979 Japan .

*Primary Examiner*—Glennon H. Hollrah
*Assistant Examiner*—Susan P. Treanor
*Attorney, Agent, or Firm*—Oblon, Fisher, Spivak, McClelland & Maier

[57] ABSTRACT

A novel plant growth regulator composition comprises a salt of 1,2-dihydropyridazine-3,6-dione and an ammonium alkylsulfate as an adjuvant at a molar ratio of 1/0.02 to 1/0.5.

The above composition has remarkable supressing actions for sucker growth, sprouting and twing growth, and allows only a very small amount of hydrazine formation during a long preservation term. The composition can thus be safely applied to edible plants.

2 Claims, No Drawings

PLANT GROWTH REGULATOR COMPOSITION

BACKGROUND OF THE INVENTION

1. Field of the Invention

This invention relates to a plant growth regulator composition and more particularly, to a plant growth regulator composition which is improved in stability of the formulation containing a salt of 1,2-dihydropyridazine-3,6-dione (hereinafter referred to as MH).

2. Description of the Prior Art

Heretofore, salts of MH have been used as an inhibitor for sucker growth in tobacco plants, an inhibitor for sprouting in potatoes, onions and the like and an inhibitor for development of strong-growing twigs in fruit trees.

Formulations of MH are now commercially sold in the form comprising a salt of MH, water and a surface active agent which is added in order to increase biological efficacies.

When, however, this type of formulation is preserved over a long term, a salt of MH is sometimes partially decomposed, thereby causing hydrazine ($NH_2$—$NH_2$) to form. Although the content of formed hydrazine is very small as below 1 ppm, this problem has to be solved on application to edible plants.

SUMMARY OF THE INVENTION

The present inventors made intensive studies to solve the above problem and, as a result, found that the formation of hydrazine could be unexpectedly suppressed when a predetermined amount of an ammonium alkylsulfate is formulated with a salt of MH, while keeping good biological effects of the resulting formulation. The present invention was accomplished on the basis of the above finding.

According to the present invention, there is provided a plant growth regulator composition which is characterized by comprising a salt of MH and an ammonium alkylsulfate as an adjuvant at a molar ratio of 1/0.02 to 1/0.5.

DETAILED DESCRIPTION OF THE INVENTION AND PREFERRED EMBODIMENTS

The salt of MH, which is an active ingredient of the plant growth regulator composition of the invention, is preferably a choline salt or a potassium salt. Of these, the choline salt of MH is preferred because choline is widely distributed in animals and plant bodies and has less toxicity, strong affinity and permeability for plants and has good translocatability in plant bodies.

The ammonium alkylsulfates used as the adjuvant should preferably have an alkyl group having from 8 to 22 carbon atoms.

In the practice of the invention, it is essential that the molar ratio of the salt of MH and the ammonium alkylsulfate be within the range of from 1/0.02 to 1/0.5. If ammonium alkylsulfates are used in excess, leaves of tobaccos and fresh leaves of mandarin oranges and peaches are liable to be chemically injured, whereas less amounts cannot suppress formation of hydrazine.

The formulated composition of this invention, containing the salt of MH and the ammonium alkylsulfate are formulated in a predetermined molar ratio, has not only remarkable effects of suppressing sucker growth, sprouting and twigs growth, but also long-term stability itself. If sodium alkylsulfates or triethanolamine alkylsulfates is used instead of ammonium alkylsulfate, the remarkable effects of the invention cannot be obtained.

The plant growth regulator composition of the invention is prepared by dissolving a mixture of a salt of MH and an ammonium alkylsulfate at an afore-indicated molar ratio in a liquid medium such as water. For the preparation, there may be added additives such as hydrophilic solvents including lower alcohols such as methanol, ethanol, isopropanol and the like, and lower alcohol ethers of glycols such as methyl cellosolve, ethyl cellosolve, butyl cellosolve, methyl carbitol, ethyl carbitol, butyl carbitol and the like; turbidity inhibitors at low temperatures such as urea, glycerine, polyethylene glycol (molecular weight of up to 1000), polypropylene glycol (molecular weight of up to 1000) and the like; defoaming agents such as methyl silicone, alkyl phosphates, fatty acids and the like; and polyoxyethylene oleyl ether.

The composition of the invention is preferably applied by providing a concentrated solution containing, for instance, from 30 to 55 wt% of the MH salt and, upon application, diluting it with water to 1:30 to 150, preferably from 1:60 to 150, as an inhibitor for sucker growth in tobacco, 1:60 to 200 as an inhibitor for sprouting in onion and potato, and 1:30 to 200 as an inhibitor for development of strong growing twigs in fruit trees.

The composition of the invention has remarkable suppressing actions for sucker growth, sprouting and twig growth, and allows only a very small amount of hydrazine being formed when preserved over a long term. The composition can thus be safely applied to edible plants.

The present invention is described with reference to the following examples.

EXAMPLE 1

Compositions of the present invention were allowed to stand in a thermostatic chamber at 40° C. for 50 days and a content of hydrazine in each composition was quantitatively determined according to the following method.

6.5 g of a composition of the invention was accurately weighed in a 50 ml volumetric flask, to which 20 ml of 1N HCl was added and agitated, followed by permitting MH to crystallize, cooling and making the whole content of the flask to 50 ml with use of pure water. Thereafter, the solution was filtered through a filter paper. 25 ml of the resultant filtrate and 10 ml of a p-dimethylaminobenzaldehyde solution were added to a 50 ml volumetric flask, and cooled, followed by addition of 0.1N HCl to bring it to a total volume of 50 ml.

The absorbance of the solution at 458 nm was measured and the content of hydrazine was obtained from a working curve and the following equation. The results are shown in Table 1.

An MH-choline salt (MH-C) stock used was an aqueous solution of 58.8 wt% MH-C (30.5% as MH).

$$\text{Content of hydrazine (ppm)} = \frac{\text{amount of hydrazine obtained from the working curve } (\mu g)}{\text{amount of sample (g)} \times (25/50)}$$

Upon calculation of the molar ratio in Table 1, the molecular weight of MH-C was taken as 215, that of ammonium laurylsulfate was as 283 and that of triethanolamine laurylsulfate was as 415.

TABLE 1

| MH-C stock (parts by weight) | Adjuvant (parts by weight) | Adjuvant (kind and mixing ratio) (wt %) | Molar ratio of MH-choline and ammonium laurylsulfate or triethanolamine laurylsulfate (MH-choline taken as 1) | Hydrazine (ppm) |
|---|---|---|---|---|
| \multicolumn{5}{c}{Control} | | | | |
| 100 | 0 | nil | 1:0 | 0.86 |
| 70 | 30 | nil (30 parts by weight of water added) | 1:0 | 0.60 |
| \multicolumn{5}{c}{Inventive Compositions} | | | | |
| 70 | 30 | ammonium laurylsulfate/methanol = 80/20 | 1:0.443 | 0.10 |
| 70 | 30 | ammonium laurylsulfate/water/methanol = 40/40/20 | 1:0.221 | 0.09 |
| 70 | 30 | ammonium laurylsulfate/water/methanol = 20/60/20 | 1:0.110 | 0.02 |
| 70 | 30 | ammonium laurylsulfate/water/methanol = 5/75/20 | 1:0.028 | 0.04 |
| 70 | 30 | ammonium laurylsulfate/polyoxyethylene ($\bar{p}$ = 13) oleyl ether/water/methanol = 40/10/30/20 | 1:0.221 | 0.08 |
| \multicolumn{5}{c}{Comparative Compositions} | | | | |
| 70 | 30 | ammonium laurylsulfate 100% | 1:0.553 | 0.65 |
| 70 | 30 | ammonium laurylsulfate/water/methanol = 1/75/20 | 1:0.0055 | 0.67 |
| 70 | 30 | ammonium laurylsulfate/polyoxyethylene ($\bar{p}$ = 13) oleyl ether/water/methanol = 2/10/68/20 | 1:0.0011 | 0.61 |
| 70 | 30 | triethanolamine laurylsulfate 100% | 1:0.3776 | 0.78 |
| 70 | 30 | triethanolamine laurylsulfate/water/methanol = 20/60/20 | 1:0.0752 | 0.88 |
| 70 | 30 | triethanolamine laurylsulfate/water/methanol = 10/70/20 | 1:0.0377 | 0.89 |
| 70 | 30 | triethanolamine laurylsulfate/polyoxyethylene ($\bar{p}$ = 13) oleyl ether/water/methanol = 20/10/50/20 | 1:0.0752 | 0.79 |

What is claimed is:

1. A plant growth regulator composition, comprising: a growth regulating effective amount of the choline salt of 1,2-dihydropyridazine-3,6-dione and an ammonium $C_{8-22}$ alkyl sulfate as adjuvant at a molar ratio of 1/0.02 to 1/0.5.

2. The composition of claim 1, wherein said ammonium alkyl sulfate is ammonium lauryl sulfate.

* * * * *